United States Patent [19]

Pike et al.

[11] 4,069,386
[45] Jan. 17, 1978

[54] 15-ALKYL PROSTAGLANDINS $E_1$

[75] Inventors: John E. Pike; William P. Schneider, both of Kalamazoo, Mich.

[73] Assignee: The Upjohn Company, Kalamazoo, Mich.

[21] Appl. No.: 655,796

[22] Filed: Feb. 6, 1976

Related U.S. Application Data

[60] Continuation of Ser. No. 525,692, Nov. 21, 1974, abandoned, which is a continuation of Ser. No. 412,054, Nov. 2, 1973, abandoned, which is a division of Ser. No. 288,618, Sept. 13, 1972, Pat. No. 3,855,270, which is a continuation of Ser. No. 37,308, May 14, 1970, abandoned, which is a continuation-in-part of Ser. No. 648,992, June 26, 1967, abandoned.

[51] Int. Cl.$^2$ ............................................. G07C 177/00
[52] U.S. Cl. ................................. 560/121; 260/514 D
[58] Field of Search ........................ 260/468 D, 514 D

[56] References Cited

U.S. PATENT DOCUMENTS

| 3,290,226 | 12/1966 | Beal et al. | 145/30 |
| 3,514,383 | 5/1970 | Beal et al. | 204/158 |
| 3,728,382 | 4/1973 | Bundy | 260/514 |

FOREIGN PATENT DOCUMENTS

| 717,178 | 12/1968 | Belgium | 260/468 |

OTHER PUBLICATIONS

Corey et al., J.A.C.S., 90, 3245 (1968).

Primary Examiner—Robert Gerstl

[57] ABSTRACT

Prostaglandin $E_1$-type and $F_1$-type compounds with a methyl or an ethyl substituent at the C-15 position are disclosed. These are useful for the same pharmacological purposes as the unsubstituted prostaglandins.

3 Claims, No Drawings

15-ALKYL PROSTAGLANDINS E₁

CROSS REFERENCE TO RELATED APPLICATION

This application is a continuation of copending application Ser. No. 525,692, filed Nov. 21, 1974, and now abandoned, which is a continuation of copending application Ser. No. 412,054, filed Nov. 2, 1973, and now abandoned, which is a division of copending application Ser. No. 288,618, filed Sept. 13, 1972, and now U.S. Pat. No. 3,855,270, which is a continuation of copending application Ser. No. 37,308, filed May 14, 1970, and now abandoned, which is a continuation-in-part of copending application Ser. No. 648,992, filed June 26, 1967, and now abandoned.

DESCRIPTION OF THE INVENTION

This invention relates to novel compositions of matter, to novel methods for producing those, and to novel chemical intermediates useful in those processes. In particular, this invention relates to novel derivatives of prostanoic acid which has the following structure and atom numbering:

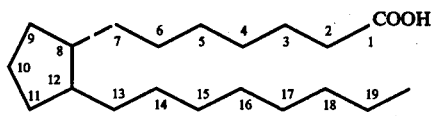

I

Various derivatives of prostanoic acid are known in the art. These are called prostaglandins. See, for example, Bergstrom et al., Pharmacol. Rev. 20, 1 (1968), and references cited therein. For example, prostaglandin E₁ (PGE₁) has the following structure:

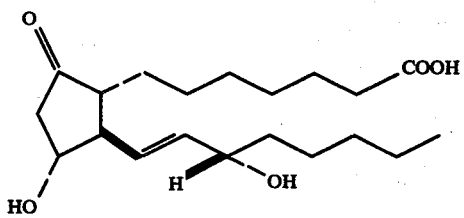

II

Prostaglandin F$_{1\alpha}$ (PGF$_{1\alpha}$) has the following structure:

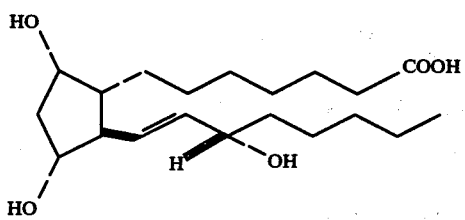

III

Prostaglandin F$_{1\beta}$ (PGF$_{1\beta}$) has the following structure:

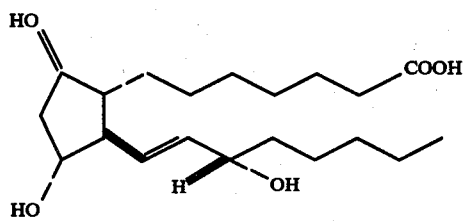

IV

In formulas II to IV, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring. The side-chain hydroxy at C-15 in formulas II to IV is in S configuration. See Nature, 212, 38 (1966) for discussion of the stereochemistry of the prostaglandins.

Molecules of the known prostaglandins each have several centers of asymmetry, and can exist in racemic (optically inactive) form and in either of the two enantiomeric (optically active) forms, i.e., the dextrorotatory and levorotatory forms. As drawn, formulas II to IV each represent the particular optically active form of the prostaglandin which is obtained from certain mammalian tissues, for example, sheep vesicular glands, swine lung, or human seminal plasma, or by carbonyl and/or double bond reduction of a prostaglandin so obtained. See, for example, Bergstrom et al., cited above. The mirror image of each of formulas II to IV would represent the other enantiomer of that prostaglandin. The racemic form of a prostaglandin would contain equal numbers of both enantiomeric molecules, and one of formulas II to IV and the mirror image of that formula would both be needed to represent correctly the corresponding racemic prostaglandin. For convenience hereinafter, use of the terms PGE₁, PGF$_{1\alpha}$, and PGF$_{1\beta}$ will mean the optically active form of that prostaglandin with the same absolute configuration as PGE₁ obtained from mammalian tissues. When reference to the racemic form of one of those prostaglandins is intended, the word "racemic" will preceed the prostaglandin name, thus, racemic PGE₁ or racemic PGF$_{1\alpha}$.

Each of the novel prostanoic acid derivatives of this invention is encompassed by the following formula or by the combination of that formula and its mirror image:

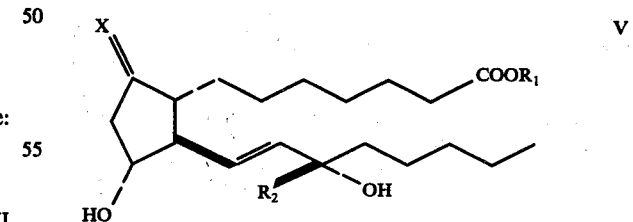

V

In formula V, R₁ is hydrogen, alkyl of one to 8 carbon atoms, inclusive, or a pharmacologically acceptable cation, R₂ is methyl or ethyl, and X is oxo, alpha hydroxy, or beta hydroxy, i.e., =O,

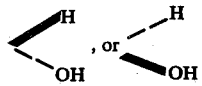

In formula V, the configuration of the hydroxy at C-15 is S as in the known prostaglandins of formulas II to IV.

A significant characteristic of all of the known prostaglandins is the secondary hydroxy group at C-15, i.e., the atom grouping

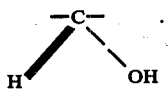

Prostaglandins obtained from animal tissues always contain that atom grouping. In striking contrast, each of the novel prostanoic acid derivatives of this invention has a tertiary hydroxy group at C-15, i.e., the atom grouping

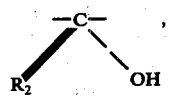

wherein $R_2$ is methyl or ethyl. Thus, these novel prostanoic acid derivatives may conveniently be designated 15-methyl-prostaglandins or 15-ethyl-prostaglandins, e.g., 15-methyl-PGE$_1$ and 15-ethyl-PGF$_{1\alpha}$.

As in the case of formulas II to IV, formula V is intended to represent optically active prostanoic acid derivatives with the same absolute configuration as PGE$_1$ obtained from mammalian tissues. The novel prostanoic acid derivatives of this invention also include the corresponding racemic compounds. Formula V plus its mirror image are necessary in combination to describe a racemic compound. For convenience hereinafter, when the word "racemic" preceeds the name of one of the novel prostanoic acid derivatives of this invention, the intent is to designate a racemic compound represented by the combination of the appropriate formula V and the mirror image of that formula. When the word "racemic" does not preceed the compound name, the intent is to designate an optically active compound represented only by the appropriate formula V and with the same absolute configuration as PGE$_1$ obtained from animal tissues.

PGE$_1$, PGF$_{1\alpha}$, and PGF$_{1\beta}$, and their esters and pharmacologically acceptable salts are extremely potent in causing various biological responses. For that reason, these compounds are useful for pharmacological purposes. See, for example, Bergstrom et al., Pharmacol. Rev. 20, 1 (1968), and references cited therein. A few of those biological responses are systemic arterial blood prssure lowering in the case of the PGE and PGF$_\beta$ compounds as measured, for example, in anesthetized (pentobarbital sodium) pentolinium-treated rats with indwelling aortic and right heart cannulas; pressor activity, similarly measured, for the PGF$_\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE compounds as shown in dogs with secretion stimulated by food or histamine infusion; activity on the central nervous system; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, PGF$_\alpha$, and PGF$_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$_\alpha$, and PGF$_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore $PGE_1$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 µg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE and $PGF_\beta$ compounds are useful as hypotensive agents to reduce blood pressure in mammals, including man. For this purpose, the compounds are administered by intravenous infusion at the rate about 0.01 to about 50 µg. per kg. of body weight per minute, or in single or multiple doses of about 25 to 500 µg. per kg. of body weight total per day.

The PGE, $PGF_\alpha$, and $PGF_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose 0.01 to 50 µg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started.

The $PGF_\alpha$ and $PGE_\beta$ compounds are useful for controlling the reproductive cycle in ovulating female mammals, including humans and animals such as monkeys, rats, rabbits, dogs, cattle, and the like. For that purpose, $PGE_1$ or $PGF_{1\alpha}$, for example, is administered systemically, e.g., intravenously, subcutaneously, and intravaginally, at a dose level in the range 0.001 mg. to about 200 mg. per kg. of body weight of the female mammal, advantageously during a span of time starting approximately at the time of ovulation and ending approximately at the next expected time of menses or just prior to that time. Additionally, expulsion of an embryo or fetus is accomplished by similar administration of the compound during the first third of the normal mammalian gestation period.

As mentioned above, the PGE compounds are potent antagonists of epinephrine-induced mobilization of free fatty acids. For this reasons, these compounds are useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The novel 15-methyl and 15-ethyl prostaglandin analogs encompassed by formula V each cause the same biological responses described above for the corresponding known prostaglandins. Each of these 15-methyl and 15-ethyl compounds is accordingly useful for the above-described pharmacological purposes, and is used for those purposes as described above. However, each of these 15-methyl and 15-ethyl prostaglandin analogs is surprisingly and unexpectedly more useful than the corresponding known prostaglandin for at least one of the pharmacological purposes described above because for that purpose the analog is more potent and has a substantially longer duration of activity. For that reason, fewer and smaller doses of these prostaglandin analogs are needed to attain the desired pharmacological results.

Novel PGE-type, PGFα-type, and PGFβ-type analogs encompassed by formula V are used as described above in the free acid form, in alkyl ester form, or in pharmacologically acceptable salt form. When the ester form is used, any alkyl ester can be used wherein the alkyl moiety contains one to 8 carbon atoms, inclusive, i.e., methyl, ethyl, propyl, butyl, pentyl, hexyl, heptyl, octyl, and isomeric forms thereof. However, it is preferred that the ester be alkyl of one to four carbon atoms, inclusive. Of those alkyl, methyl and ethyl are especially preferred for optimum absorption of the compound by the body or experimental animal system.

Pharmacologically acceptable salts of these prostaglandin analogs useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethymorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1- butanol, 2amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

As discussed above, the prostaglandin analogs are administered in various ways for various purposes; e.g., intravenously, intramuscularly, subcutaneously, orally, intravaginally, rectally, buccally, sublingually, topically, and in the form of sterile implants for prolonged action.

For intravenous injection or infusion, sterile aqueous isotonic solutions are preferred. For that purpose, it is preferred because of increased water solubility to use the free acid form of the pharmacologically acceptable salt form. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral or sublingual administration. For rectal or vaginal administration, suppositories, tampons, ring devices, and preparations adapted to generate sprays or foams or to be used for lavage, all prepared as known in the art, are used. For tissue implants, a sterile tablet or silicone rubber capsule or other object containing or impregnated with the substance is used.

The novel PGF$_{1\alpha}$-type and PGF$_{1\beta}$-type acids and esters of formula V wherein X is

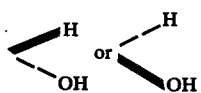

are prepared by the sequence of transformations shown in Chart A, wherein formulas VII, VIII, IX, X, and XI include optically active compounds as shown and racemic compounds of those formulas and the mirror image thereof. Also in Chart A, R$_2$ is methyl or ethyl, R$_4$ is hydrogen or alkyl of one to 8 carbon atoms, inclusive, and ~ indicates attachment of hydroxy to the ring in alpha or beta configuration. Also in Chart A, A is alkyl of one to 4 carbon atoms, inclusive, aralkyl of 7 to 12 carbon atoms, inclusive, phenyl, or phenyl substituted with one or 2 fluoro, chloro, or alkyl of one to 4 carbon atoms, inclusive, and R$_3$ is alkyl of one to 8 carbon atoms, inclusive, or —Si—(A)$_3$ wherein A is as defined above. The various A of a —Si(A)$_3$ moiety are alike or different. For example, an —Si(A)$_3$ can be trimethylsilyl, dimethylphenylsilyl, or methylphenylbenzylsilyl. Examples of alkyl of one to 4 carbon atoms, inclusive, are methyl, ethyl, propyl, isopropyl, butyl, isobutyl, sec-butyl, and tert-butyl. Examples of aralkyl of 7 to 12 carbon atoms, inclusive, are benzyl, phenethyl, α-phenylethyl, 3-phenylpropyl, α-napthylmethyl, and 2-(β-naphthyl)ethyl. Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tert-butylphenyl, 4-chloro-2-methylphenyl, and 2,4-dichloro-3-methylphenyl.

CHART A

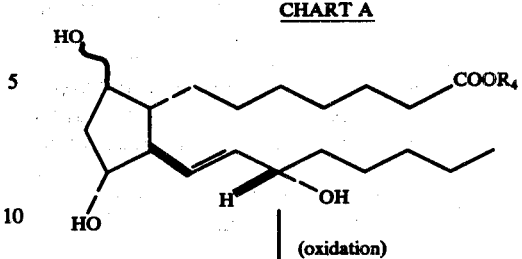

VII

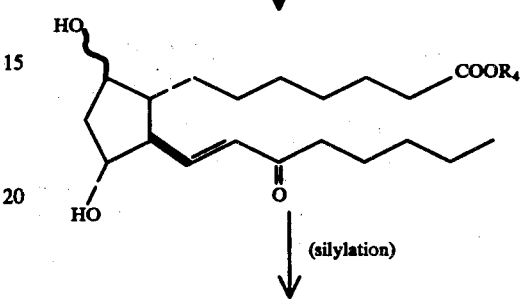

VIII

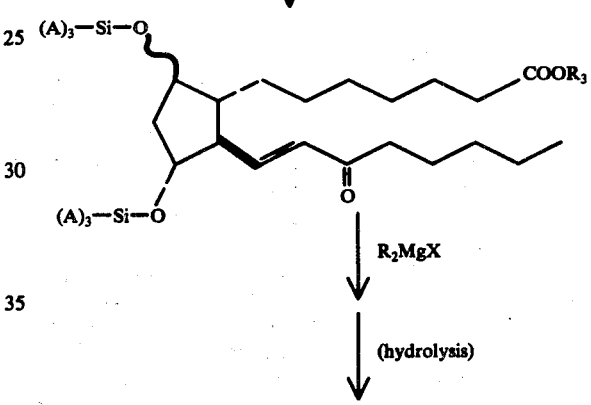

IX

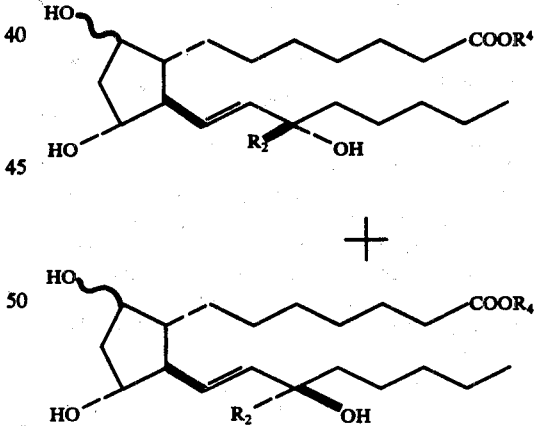

X

+

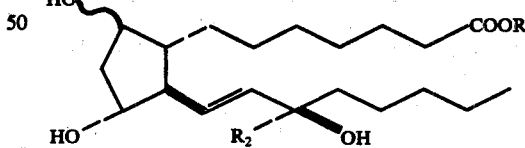

XI

In Chart A, the final novel PGF$_{1\alpha}$ and PGF$_{1\beta}$ acid and ester analogs of this invention are encompassed by formula X.

The initial optically active reactants of formula VII in Chart A, i.e., PGF$_{1\alpha}$ and PGF$_{1\beta}$, and their alkyl esters are known in the art or are prepared by methods known in the art. See, for example, Bergstrom et al., cited above, and U.S. Pat. No. 3,069,322. The initial racemic reactants of formula VII in Chart A, i.e., racemic PGF$_{1\alpha}$, racemic PGF$_{1\beta}$, and alkyl esters of those are also known in the art or are prepared by methods known in the art. See, for example, Just et al., J. Am.

Chem. Soc. 91, 5364 (1969) and Corey et al., J. Am. Chem. Soc. 90, 3245 (1968).

The known acids and esters of formula VII are transformed to the corresponding intermediate 15-oxo acids and esters of formula VIII by oxidation with reagents such as 2,3-dichloro-5,6-dicyano-1,4-benzoquinone, activated manganese dioxide, or nickel peroxide (see Fieser et al., "Reagents for Organic Synthesis," John Wiley & Sons, Inc., New York, N.Y., pp. 215, 637, and 731). These reagents are used according to procedures known in the art.

Referring again to Chart A, the intermediate compounds of formula VIII are transformed to silyl derivatives of formula IX, respectively, by procedures known in the art. See, for example, Pierce, "Silylation of Organic Compounds," Pierce Chemical Co., Rockford, Ill. (1968). Both hydroxy groups of the formula VIII reactants are thereby transformed to —O—Si—(A)$_3$ moieties wherein A is as defined above, and sufficientt of the silylating agent is used for that purpose according to known procedures. When R$_4$ in the formula VIII intermediate is hydrogen, the —COOH moiety thereby defined is simultaneously transformed to —COO—Si—(A)$_3$, additional silylating agent being used for this purpose. This latter transformation is aided by excess silylating agent and prolonged treatment. When R$_4$ in formula VIII is alkyl, then R$_3$ in formula IX will also be alkyl. The necessary silylating agents for these transformations are known in the art or are prepared by methods known in the art. See, for example, Post, "Silicones and Other Organic Silicon Compounds," Reinhold Publishing Corp., New York, N.Y. (1949).

Referring again to Chart A, the intermediate silyl compounds of formula IX are transformed to the final compounds of formulas X + XI by first reacting the silyl compound with a Grignard reagent of the formula R$_2$MgX wherein R$_2$ is methyl or ethyl, and X is chloro, bromo, or iodo. For this purpose, it is preferred that X be bromo. This reaction is carried out by the usual procedure for Grignard reactions, using diethyl ether as a reaction solvent and saturated aqueous ammonium chloride solution to hydrolyze the Grignard complex. The resulting disilyl or trisilyl tertiary alcohol is then hydrolyzed with water to remove the silyl groups. For this purpose, it is advantageous to use a mixture of water and sufficient of a water-miscible solvent, e.g., ethanol, to give a homogeneous reaction mixture. The hydrolysis is usually complete in 2 to 6 hours at 25° C., and is preferably carried out in an atmosphere of an inert gas, e.g., nitrogen or argon.

The mixture of 15-S and 15-R isomers obtained by this Grignard reaction and hydrolysis is separated by procedures known in the art for separating mixtures of prostanoic acid derivatives, for example, by chromatography on neutural silica gel. In some instances, the lower alkyl esters, especially the methyl esters of a pair of 15-S and 15-R isomers are more readily separated by silica gel chromatography than are the corresponding acids. In those cases, it is advantageous to esterify the mixture of acids as described below, separate the two esters, and then, if desired, saponify the esters by procedures known in the art for saponification of prostaglandinds F.

The novel optically PGE$_1$-type acids and esters of formula V wherein X is =O are prepared by oxidation of the corresponding S PGF$_{1\alpha}$-type or PGF$_{1\beta}$-type acids and alkyl esters of formula X. For this purpose, an oxidizing agent is used which selectively oxidizes secondary hydroxy groups to carbonyl groups in the presence of carbon-carbon double bonds. These transformations are shown in Chart B wherein formulas X and XII include optically active compounds as shown and racemic compounds of those formulas and the mirror images thereof. Also in Chart B, R$_2$ is methyl or ethyl, R$_4$ is hydrogen or alkyl of one to 8 carbon atoms, inclusive, and $\sim$ indicates attachment of hydroxy to the ring in alpha or beta configuration. The reactants and products of formulas X and XII each have the 15-hydroxy in S configuration.

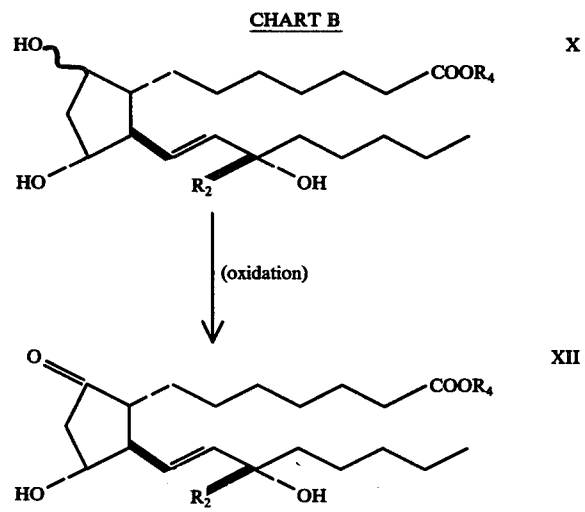

For the transformation of Chart B, the beta isomers of reactants X are preferred starting materials, although the corresponding alpha isomers are also useful for this purpose.

Oxidation reagents useful for the transformations set forth in Chart B are known to the art. An especially useful reagent for this purpose is the Jones reagent, i.e., acidified chromic acid. See J. Chem. Soc. 39 (1946). Acetone is a suitable diluent for this purpose, and a slight excess beyond the amount necessary to oxidize one of the secondary hydroxy groups of the formula X reactant is used. Reaction temperatures at least as low as about 0° C. should be used. Preferred reaction temperatures are in the range −10° to −50° C. The oxidation proceeds rapidly and is usually complete in about 5 to 20 minutes. The excess oxidant is destroyed, for example, by addition of a lower alkanol, advantageously, isopropyl alcohol, and the formula XII PGE-type product is isolated by conventional methods.

Examples of other oxidation reagents useful for the Chart B transformations are silver carbonate on Celite (Chem. Commun. 1102 (1969)), mixtures of chromium trioxide and pyridine (Tetrahedron Letters 3363 (1968), J. Am. Chem. Soc. 75, 422 (1953), and Tetrahedron, 18, 1351 (1962)), mixtures of sulfur trioxide in pyridine and dimethyl sulfoxide (J. Am. Chem. Soc. 89, 5505 (1967)), and mixtures of dicyclohexylcarbodiimide and dimethyl sulfoxide (J. Am. Chem. Soc. 87, 5661 (1965)).

As discussed above, the processes of Charts A and B lead either to acids (R$_4$ is hydrogen) or to alkyl esters (R$_4$ is alkyl of one to 8 carbon atoms, inclusive). When a formula X PGF$_1$-type acid or a formula XII PGE$_1$-type acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, for example, gives the ethyl, butyl, and 2-ethylhexyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley & Sons, Inc., New York, N.Y., Vol. 8, pp. 389–394 (1954).

An alternative method for esterification of the carboxyl moiety of the PGF-type or PGE-type compounds comprises transformation of the free acid to the corresponding silver salts, followed by interaction of that salt with an alkyl iodide. Examples of suitable iodides are methyl iodide, ethyl iodide, butyl iodide, iosbutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The novel formula X and XII acids ($R_1$ is hydrogen) are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt of the prostanoic acid derivative. Evaporation of the water or addition of a water-miscible solvent of moderate polarity, for example, a lower alkanol or a lower alkanone, gives the solid inorganic salt if that form is desired.

To produce an amine salt, the acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the acid with the stoichiometric amount of the corresponding quaternary ammonium hydroxide in water solution, followed by evaporation of the water.

The optically active and racemic forms of 15-methyl-$PGE_1$, 15-ethyl-$PGE_1$, 15-methyl-$PGF_{1\alpha}$, and 15-ethyl-$PGF_{1\alpha}$ are also prepared by the processes set forth and described in copending application Ser. No. 648,991, filed June 26, 1967. Those processes use as initial reactants, all-cis 15-methyl-8,11,14-eicosatrienoic acid to produce these 15-methyl prostaglandin analogs, and all-cis 15-ethyl-8,11,14-eicosatrienoic acid to produce these 15-ethyl prostaglandin analogs. The preparation of all-cis 15-methyl-8,11,14-eicosatrienoic acid is set forth and described in said copending application. Use of 3-octanone in place of the 2-heptanone used as initial reactant in that process leads to all-cis 15-ethyl-8,11,14-eicosatrienoic acid.

As set forth and described in said copending application, all-cis 15-methyl-8,11,14-eicosatrienoic acid and all-cis 15-ethyl-8,11,14-eicosatrienoic acid are each transformed to racemic 15-methyl-$PGE_1$ or racemic 15-methyl-$PGF_{1\alpha}$ and to racemic 15-ethyl-$PGE_1$ or racemic 15-ethyl-$PGF_{1\alpha}$, respectively, by reacting said acids with singlet oxygen and then treating the resulting product with a reducing agent to produce $PGF_\alpha$-type analogs or with a mild reducing agent and then with a base, a metal ion catalyst, or with ultraviolet light to produce the PGE-type analogs.

The optically active prostaglandin analogs, 15-methyl-$PGE_1$, 15-methyl-$PGF_{1\alpha}$, 15-ethyl-$PGE_1$, and 15-ethyl-$PGF_{1\alpha}$ are prepared as set forth and described in said copending application by resolution of the corresponding racemic forms prepared as described above. Alternatively, as set forth and described in said copending application, these optically active acids are prepared by aerobic incubation of all-cis 15-methyl-8,11,14-eicosatrienoic acid or all-cis 15-ethyl-8,11,14-eicosatrienoic acid with comminuted sheep vesicular gland tissue or with the enzyme system contained therein, in a substantially aqueous medium. For additional procedural details, see also U.S. Pat. No. 3,296,091, Kupiecki, Life Sciences, 4, 1811 (1965), Struijk, Rec. Trav. Chim. 85, 1233 (1966), and Nugteren et al., Rec. Trav. Chim., 85, 405 (1966).

These biological oxidations produce mixtures of 15-methyl-$PGE_1$ and 15-methyl-$PGF_{1\alpha}$ and of 15-ethyl-$PGE_1$ and 15-ethyl-$PGF_{1\alpha}$. The components of these mixtures are separated and each component is purified as set forth in U.S. Pat. No. 3,296,091, or by other procedures known to be useful for separating mixutes of the known prostaglandins and purifying the individual components. In particular, advantage is taken of the greater polarity of the $PGF_{1\alpha}$-type compound in comparison wih the $PGE_1$-type compound in these separations, using chromatography on acid-washed silica gel, reversed phase partition chromatography, preparative thin layer chromatography, or countercurrent distribution, or a combination of those.

When 15-methyl-$PGF_{1\beta}$ or 15-ethyl-$PGF_{1\beta}$ is the desired product, that is prepared along with additional amounts of 15-methyl-$PGF_{1\alpha}$ or 15-ethyl-$PGF_{1\alpha}$ by ring carbonyl reduction of 15-methyl-$PGE_1$ or 15-ethyl-$PGE_1$. For this purpose, any reducing agent is used which does not react with carbon-carbon double bonds or acid or ester groups. Preferred reagents are lithium (tri-tert-butoxy)aluminum hydride, the metal borohydrides, especially sodium, potassium, and zinc borohydrides, and the metal trialkoxy borohydrides, e.g., sodium trimethoxyborohydride. The mixtures of alpha and beta reduction products are separated into the individual alpha and beta isomers by methods known in the art for the separation of analogous pairs of known isomeric prostaglandins. See, for example, Bergstrom et al., Arkiv for Kemi, 19, 563 (1963), Acta Chem. Scand., 16, 969 (1962), and British Specification No. 1,097,533. See also Granstrom et al., J. Biol Chem., 240, 457 (1965) and Green et al., J. Lipid Research, 5, 117 (1964). Especially preferred as separation methods are partition chromatographic procedures, both normal and reversed phase, preparative thin layer chromatography, and countercurrent distribution procedures.

When alkyl esters or salts of these $PGE_1$-type, $PGF_{1\alpha}$-type, or $PGF_{1\beta}$-type acid analogs are desired, those are prepared by alkyl esterification or salt formation as described above.

The invention can be more fully understood by the following examples

Infrared absorption spectra are recorded on a Perkin-Elmer model 421 infrared spectrophotometer. Undiluted (neat) samples of the liquids and oils are used. Mineral oil (Nujol) mulls of the solids are used.

NMR spectra are recorded on a Varian A-60 spectrophotometer with tetramethylsilane as an internal standard (downfield) and using solvents as indicated below.

Mass spectra are recorded on an Atlas CH-4 mass spectrometer with a TO-4 source (ionization voltage 70ev).

The term "15-oxo-" in front of a compound name, e.g., 15-oxo-$PGF_{1\alpha}$, refers to a prostaglandin analog wherein the moiety

at the 15-position has been transformed to

EXAMPLE 1

15-Oxo-$PGF_{1\alpha}$.

2,3-Dichloro-5,6-dicyano-1,4-benzoquinone (463 mg.) is added to a solution of $PGF_{1\alpha}$ (600 mg.) in 30 ml. of dioxane. The mixture is stirred 24 hours at 50° C. under nitrogen, and then is cooled to 20° C. and filtered. The filtered solids are washed with dichloromethane. Evaporation of the combined filtrate and washings at reduced pressure gives 650 mg. of a residue which is chromatographed on 150 g. of silica gel (Silicar CC-4; Mallincrodt), eluting with 50% ethyl acetate in Skellysolve B (a mixture of isomeric hexanes). Evaportion of the eluates gives 545 mg. of 15-oxo-$PGF_{1\alpha}$; infrared absorption at 3400, 2660, 1700, 1660, 1620, 1460, 1410, 1375, 1285, 1250, 1185, 1120, 1070, and 980 cm$^{-1}$.

EXAMPLE 2

15-Oxo-$PGF_{1\beta}$.

2,3-Dichloro-5,6-dicyano-1,4-benzoquinone (1.0 g.) is added to a solution of $PGF_{1\beta}$ (1.3 g.) in 80 ml. of dioxane. The mixture is stirred 24 hours at 50° C. under nitrogen, and is then cooled to 20° C. and filtered. The filtered solids are washed with dichloromethane. Evaporation of the combined filtrate and washings at reduced pressure gives 1.6 g. of a residue which is chromatographed on 400 g. of silica gel (Silicar CC-4; Mallincrodt), eluting with 75% ethyl acetate in Skellysolve B. Evaporation of the eluates gives 1.15 g. of 15-oxo-$PGF_{1\beta}$; infrared absorption at 3380, 2660, 1720, 1705, 1665, 1620, 1460, 1405, 1370, 1325, 1285, 1235, 1190, 1080, 1040, and 980 cm$^{-1}$.

Following the procedure of Example 1, the methyl, ethyl, tert-butyl, and 2-ethylhexyl esters of $PGF_{1\alpha}$ and $PGF_{1\beta}$ are each oxidized to the corresponding 15-oxo compounds.

Also following the procedure of Example 1, the racemic forms of $PGF_{1\alpha}$ and $PGF_{1\beta}$, and the methyl, ethyl, tert-butyl, and 2-ethylhexyl esters of each of those are each oxidized to the corresponding racemic 15-oxo compound.

EXAMPLE 3

Tris-(trimethylsilyl) Derivatives of 15-Oxo-$PGF_{1\alpha}$.

A mixture of hexamethyldisilazane (11 ml.) and trimethylchlorosilane (2.2 ml.) is added to a solution of 15-oxo-$PGF_{1\alpha}$ (545 mg.) in 55 ml. of tetrahydrofuran. This mixture is stirred 16 hours at 25° C. under nitrogen, and is then filtered. The filtrate is evaporated under reduced pressure. Xylene (50 ml.) is added to the residue and the mixture is evaporated at 60° C. under reduced pressure. This addition of xylene and evaporation is repeated twice. The resulting residue is the tris-(trimethylsilyl) derivative of 15-oxo-$PGF_{1\alpha}$; infrared absorption at 1365, 1250, and 1180 cm$^{-1}$.

EXAMPLE 4

Tris-(trimethylsilyl) Derivatives of 15-Oxo-$PGF_{1\beta}$.

Following the procedure of Example 3, 15-oxo-$PGF_{1\beta}$ is transformed to the tris-(trimethylsilyl) derivative; infrared absorption at 1725, 1680, 1635, 1365, 1250, 1180, 1065, 980, 840, and 750 cm$^{-1}$.

Following the procedure of Example 3, the methyl, ethyl, tert-butyl, and 2-ethylhexyl esters of 15-oxo-$PGF_{1\alpha}$ and 15-oxo-$PGF_{1\beta}$ are each transformed to the corresponding bis-(trimethylsilyl) derivative.

Also following the procedure of Example 3, the racemic forms of 15-oxo-$PGF_{1\alpha}$ and 15-oxo-$PGF_{1\beta}$, and the methyl, ethyl, tert-butyl, and 2-ethylhexyl esters of each of those are each transformed to trimethylsilyl derivatives, the acids to tris derivatives and the esters to bis derivatives.

EXAMPLE 5

15-Methyl$PGF_{1\alpha}$.

A 3 molar diethyl ether solution of methylmagnesium bromide (0.55 ml.) is added dropwise to a stirred solution of the tris-(trimethylsilyl) derivative of 15-oxo-$PGF_{1\alpha}$ (850 mg.) in 25 ml. of diethyl ether at 25° C. The mixture is stirred 30 minutes at 25° C., after which an additional 0.2 ml. of the methylmagnesium bromide solution is added and stirring is continued an additional 30 minutes. The resulting reaction mixture is poured into 75 ml. of saturated aqueous ammonium chloride solution at 0° C. After stirring several minutes, the mixture is extracted repeatedly with diethyl ether. The combined diethyl ether extracts are washed with saturated aqueous sodium chloride solution and then dried with anhydrous sodium sulfate. Evaporation of the diethyl ether gives a yellow oil (910 mg.) which is dissolved in 45 ml. of ethanol. That solution is diluted with 30 ml. of water, and the mixture is stirred 4 hours at 25° C. The ethanol in the resulting solution is evaporated at reduced pressure, and the aqueous residue is saturated with sodium chloride and then extracted with ethyl acetate. The extract is washed with saturated aqueous sodium chloride solution, dried with anhydrous sodium sulfate, and evaporated under reduced pressure to give 640 mg. of a mixture of 15-methyl-$PGF_{1\alpha}$ and 15-methyl-15(R)-$PGF_{1\alpha}$; Infrared absorption at 3280, 2600, and 1710 cm$^{-1}$.

The mixture of 15-methyl-$PGF_{1\alpha}$ and 15-methyl-15(R)-$PGF_{1\alpha}$ is dissolved in 50 ml. of diethyl ether and cooled to 0° C. Excess diazomethane dissolved in diethyl ether is then added, and the mixture is maintained 5 minutes at 0° C. and then 5 minutes at 25° C. The solution is evaporated in a stream of nitrogen, and the residue is chromatographed on 550 g. of neutral silica, eluting with 75% ethyl acetate in Skellysolve B. Evaporation of eluate fractions gives, successively, 127 mg. of 15-methyl-15(R)-$PGF_{1\alpha}$ methyl ester, 150 mg. of a mixture of 15-methyl-15(R)-$PGF_{1\alpha}$ methyl ester and 15-methyl-$PGF_{1\alpha}$ methyl ester, and 228 mg. of 15-methyl-$PGF_{1\alpha}$ methyl ester. The latter crystallizes on standing; m.p. 72°-75° C.; mass spectral molecular ion peaks at 366, 348, 317, 313, and 294.

Aqueous potassium hydroxide solution (45%; 0.9 ml. is added to a solution of 15-methyl-$PGF_{1\alpha}$ methyl ester (228 mg.) in a mixture of 6.8 ml. of methanol and 2.2 ml. of water under nitrogen. The resulting solution is stirred 2 hours at 25° C., and is then poured into several volumes of water. The aqueous mixture is extracted with ethyl acetate, acidified with 3 N hydrochloric acid, saturated with sodium chloride, and then extracted repeatedly with ethyl acetate. The latter ethyl acetate extracts are combined, washed successively with water and saturated aqueous sodium chloride solution, dried with anhydrous sodium sulfate, and evaporated under reduced pressure. The crystalline residue is recrystallized from a mixture of ethyl acetate and Skellysolve B to give 15-methyl-$PGF_{1\alpha}$; m.p. 81°-83° C.; infrared absorption at 3410, 3300, 2650, 1705, 1305, 1290, 1275, 1255, 1220, 1195, 1125, 1075, 980, and 915 cm$^{-1}$; NMR peaks (dimethylformamide) at 5.5 and 4.4-3.6 (multiplet) δ; mass spectral molecular ion peaks at 643, 587, and 568 (tris-trimethylsilyl derivative).

EXAMPLE 6

15-Methyl-$PGF_{1\beta}$.

A 3 molar diethyl ether solution of methylmagnesium bromide (0.67 ml.) is added dropwise to a stirred solution of the tris-(trimethylsilyl) derivative of 15-oxo-$PGF_{1\beta}$ (910 mg.) in 25 ml. of diethyl ether at 25° C. The mixture is stirred 30 minutes at 25° C., after which an additional 0.3 ml. of the methylmagnesium bromide solution is added and stirring is continued an additional 15 minutes. The resulting reaction mixture is poured into a mixture of ice and 75 ml. of saturated aqueous ammonium chloride solution. After stirring several minutes, the mixture is extracted repeatedly with diethyl ether. The combined diethyl ether extracts are washed with saturated aqueous sodium chloride solution and then dried with anhydrous sodium sulfate. Evaporation of the diethyl ether at reduced pressure gives a colorless, viscous oil which is dissolved in 30 ml. of ethanol. That solution is diluted with 20 ml. of water, and the mixture is stirred 3 hours at 25° C. The ethanol in the resulting solution is evaporated at reduced pressure, and the aqueous residue is diluted with an equal volume of saturated aqueous sodium chloride solution and then extracted repeatedly with ethyl acetate. The combined extracts are washed with saturated aqueous sodium chloride solution, dried with anhydrous sodium sulfate, and evaporated at reduced pressure to give 700 mg. of a crystalline mixture of 15-methyl-$PGF_{1\beta}$ and 15-methyl-15(R)-$PGF_{1\beta}$. Recrystallization of this mixture three times from ethyl acetate containing a trace of methanol gives 15-methyl-$PGF_{1\beta}$; m.p. 164°-164.5° C; infrared absorption at 3250, 3160, 2700, 1710, 1330, 1315, 1305, 1085, 1035, and 970 cm$^{-1}$; NMR peaks (dimethylformamide) at 5.53 (doublet), 5.10-3.6 (multiplet), and 1.20 (singlet) δ; mass spectral molecular ion peaks at 370, 352, and 334.

Following the procedure of Example 5, the methyl, ethyl, tert-butyl, and 2-ethylhexyl esters of the bis-(trimethylsilyl derivatives) of $PGF_{1\alpha}$ and $PGF_{1\beta}$ are each transformed to the corresponding 15-methyl esters.

Also following the procedure of Example 5, the racemic forms of the trimethylsilyl derivatives of 15-oxo-$PGF_{1\alpha}$ and 15-oxo-$PGF_{1\beta}$, and the methyl, ethyl, tert-butyl, and 2-ethylhexyl esters of each of those, tris derivatives of the acids and bis derivatives of the esters, are each transformed to the corresponding 15-methyl acid or esters.

Also following the procedure of Example 5 but using ethylmagnesium bromide in place of methylmagnesium bromide, the tris-(trimethylsilyl) derivatives of $PGF_{1\alpha}$ and $PGF_{1\beta}$, and the racemic form of each of those optically active acids, and also the bis-(trimethylsilyl) derivative of the methyl, ethyl, tert-butyl, and 2-ethylhexyl ester of each of those optically active and racemic acids are each transformed to the corresponding 15-ethyl acid or ester.

EXAMPLE 7

15-Methyl-$PGE_1$.

A solution of 15-methyl-$PGF_{1\beta}$ (95 mg.) in 40 ml. of acetone is cooled to −10° C. Jones reagent (0.1 ml. of a solution of 21 g. of chromic anhydride, 60 ml. of water, and 17 ml. of concentrated sulfuric acid), precooled to 0° C., is added with vigorous stirring. After 5 minutes at −10° C., thin layer chromatography on silica gel (acetic acid: methanol : chloroform; 5:5:90) of a small portion of the reaction mixture indicates about 50% reaction completion. An additional 0.06 ml. of Jones reagent is added to the still cold reaction mixture with stirring, and the mixture is stirred an additional 5 minutes at −10° C. Isopropyl alcohol (1 ml.) is added to the cold reaction mixture. After 5 minutes, the mixture is filtered through a layer of diatomaceous silica (Celite). The filtrate is evaporated at reduced pressure, and the residue is mixed with 5 ml. of saturated aqueous sodium chloride solution. The mixture is extracted repeatedly with ethyl acetate, and the combined extracts are washed with saturated aqueous sodium chloride solution, dried with anhydrous sodium sulfate, and evaporated at reduced pressure. The residue is chromatographed on 20 g. of neutral silica gel, eluting with 50% ethyl acetate in Skellysolve B. Evaporation of the eluates gives 29 mg. of 15-methyl-$PGE_1$; mass spectral molecular ion peaks at 350, 332, 317, and 261.

Following the procedure of Example 7, 15-methyl-$PGF_{1\alpha}$ is oxidized to 15-methyl-$PGE_1$.

Also following the procedure of Example 7, the methyl, ethyl, tert-butyl, and 2-ethylhexyl esters of 15-methyl-PGF$_{1\alpha}$ and 15-methyl-PGF$_{1\beta}$ are each oxidized to the corresponding 15-methyl-PGE$_1$ ester.

Also following the procedure of Example 7, the racemic forms of 15-methyl-PGF$_{1\alpha}$ and 15-methyl-PGF$_{1\beta}$, and the methyl, ethyl, tert-butyl, and 2-ethylhexyl esters of each of those racemic acids are each oxidized to the corresponding 15-methyl-PGE$_1$ acid or ester.

Also following the procedure of Example 7, 15-ethyl-PGF$_{1\alpha}$ and 15-ethyl-PGF$_{1\beta}$, and the racemic forms of each of those optically active acids, and the methyl, ethyl, tert-butyl, and 2-ethylhexyl ester of each of those optically active and racemic acids are each oxidized to the corresponding 15-ethyl-PGE$_1$ acid or ester.

We claim:

1. An optically active compound of the formula:

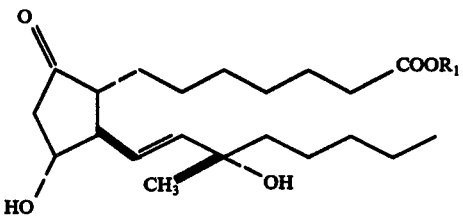

wherein R$_1$ is hydrogen, alkyl of one to 8 carbon atoms, inclusive, or a pharmacologically acceptable cation.

2. 15-Methyl-PGE$_1$, an optically active compound according to claim 1 wherein R$_1$ is hydrogen.

3. 15-Methyl-PGE$_1$ methyl ester, an optically active compound according to claim 1 wherein R$_1$ is methyl.

* * * * *